United States Patent [19]

Rawson

[11] Patent Number: 5,436,444
[45] Date of Patent: * Jul. 25, 1995

[54] MULTIMODE OPTICAL FIBER MOTION MONITOR WITH AUDIBLE OUTPUT

[75] Inventor: Eric G. Rawson, Saratoga, Calif.

[73] Assignee: Alamed Corporation, Portola Valley, Calif.

[ * ] Notice: The portion of the term of this patent subsequent to Mar. 1, 2011 has been disclaimed.

[21] Appl. No.: 53,687

[22] Filed: Apr. 29, 1993

Related U.S. Application Data

[63] Continuation-in-part of Ser. No. 975,853, Nov. 13, 1992, Pat. No. 5,291,013, which is a continuation-in-part of Ser. No. 802,868, Dec. 6, 1991, Pat. No. 5,212,379.

[51] Int. Cl.[6] .............................................. H01J 40/14
[52] U.S. Cl. ................................ 250/227.14; 340/566; 128/691
[58] Field of Search .................... 250/227.14, 227.16, 250/227.19, 227.11; 340/555, 556, 565, 566; 128/691, 714; 389/566

[56] References Cited

U.S. PATENT DOCUMENTS 3,840,738 10/1974 Indig et al. ......................... 359/566
4,442,750 4/1984 Bowley ............................ 250/227.19
4,715,671 12/1987 Miesak ........................... 250/227.11
5,164,703 11/1992 Rickman ............................. 340/566
5,291,013 3/1994 Nafarrate et al. .

Primary Examiner—Edward P. Westin
Attorney, Agent, or Firm—Oblon, Spivak, McClelland, Maier & Neustadt

[57] ABSTRACT

A motion monitor which produces audible sound representative of motions of a subject or object being monitored, including a carrier, an optical fiber carried by the carrier, a laser source for injecting a laser beam in the optical fiber to produce a speckle light pattern at the output of the optical fiber, a photodetector for producing an output signal representative of modal noise developed in the optical fiber due to physical movement of the fiber, an amplifier for amplifying the output of the photodetector, and a loudspeaker which converts the amplified signals to audible sound representative of the modal noise at the fiber output. Optionally, the signals produced by the photodetector are shifted to a higher frequency range, e.g., the 500–700 Hz range, thereby to enable use of conventional inexpensive electronics and efficient loudspeakers. In one embodiment involving monitoring of a person, the frequency shifted output of the photodetector is transmitted to a remote location for remote monitoring of movements of the person. In another embodiment, the loudspeaker is mounted on the carrier and produces sound mimicking movement of the subject or object to which the carrier is attached.

24 Claims, 3 Drawing Sheets

MULTIMODE OPTICAL FIBER MOTION MONITOR WITH AUDIBLE OUTPUT

CROSS REFERENCE TO RELATED APPLICATIONS

This application is a continuation-in-part of U.S. patent application Ser. No. 07/975,853 filed Nov. 13, 1992 now U.S. Pat. No. 5,291,013, which is a continuation-in-part of U.S. patent application Ser. No. 07/802,868 filed Dec. 6, 1991 now U.S. Pat. No. 5,212,379.

BACKGROUND OF THE INVENTION

1. Field of the Invention

This invention relates to an audio motion monitor, and particularly a monitor for sensing the motion of a person, such as an infant or adult in a bed or crib, or a child wearing a toy costume, or an object, such as a toy, using the modal noise produced by transmitting a coherent light signal through an optical fiber.

2. Discussion of Background

Several companies make and sell audio monitors for use with infants and children. These monitors operate by means of a one-way transmission of sound using a microphone/transmitter, and typically include a base unit located close to the child to detect sounds in the area and transmit the detected sounds via a radio to a remote monitor. Typically, the remote monitor is a portable battery operated unit which can be worn on the belt of a care giver or otherwise conveniently kept near to the care giver. The conventional infant monitors are listening devices by which sounds of crying or other activity by the child can be routinely monitored remotely by the care giver.

The above-identified U.S. patent application Ser. Nos. 07/802,868 and 07/975,853, each use the modal noise induced in coherent light propagating in a multimode optical fiber in the presence of mechanical motions of a human subject to detect the subject's breathing and heartbeat. These two applications teach injecting a coherent light beam into one end of a multi-mode optical fiber and illuminating a photodetector, optimally a two-segment "split" detector, with the light emerging from the other end of the optical fiber, and processing the signals derived from the modal noise existing at the output end of the fiber to detect and quantify the subject's breathing and heartbeat. However, under certain circumstances, it may not be necessary to employ the processing necessary to detect and quantify the subject's heartbeat and breathing, and for such circumstances a simpler, lower cost approach is desirable.

SUMMARY OF THE INVENTION

Accordingly, one object of this invention is to provide a new and improved monitor by which it is possible for a care giver to monitor remotely movements of a child or infant.

Another object of this invention is to provide a low-cost monitor by which even small movements of a subject being monitored can be remotely monitored.

Yet another object of this invention is to provide a monitor which generates sounds whose amplitude and frequency vary in relation to motions of a subject being monitored.

Yet a further object of the present invention is to provide a novel article of clothing attached or coupled to a living subject, whether a living human or animal, a robot or robotic toy, a piece of machinery, or a vehicle, by which movements of the subject to which the article is attached can be audibly signaled.

Yet another object of the present invention is to provide a novel pad which can be placed, for example, on the floor and upon which various games can be conducted, the physical movements of which are rendered into novel and interesting sounds. For example, a wrestling pad, or a dance floor cover, or a jogging track, could be covered with a pad constructed according to this invention, thereby generating a novel and interesting sound accompaniment for the activities described. As another example, the game "Twister" is played on a plastic sheet with numerous large colored circles which players must contact with an arm, a leg, an elbow or knee, according to the dictates of the spin of a dial. Using a fiber motion sensor attached to this pad would add a new audible dimension to the play of that game.

These and other objects are achieved according to the present invention by providing a new and improved audio motion monitor for producing an audible signal related to movement of a subject or object to which the monitor is attached, including a carrier, an optical fiber supported by the carrier and having an input end and an output end, a laser source for injecting a coherent light beam into the input end of the fiber, a photoreceiver coupled to the output end of the fiber and illuminated by laser light transmitted through the fiber, the photoreceiver producing an output signal related to movements of the fiber, an amplifier for amplifying the output signal of the receiver, and a loudspeaker having an input to which is applied the amplified output of the photoreceiver and which produces audible sound representative of modal noise produced at the output end of the optical fiber due to movement of the optical fiber.

In a preferred embodiment, introduced between the photoreceiver and the amplifier is a frequency shifter to shift the frequency spectrum of the modal noise signal produced by the fiber to a convenient frequency range, such as 500 to 700 Hz, which can be efficiently amplified and reproduced by inexpensive audio electronics and loudspeakers.

In one embodiment for remote monitoring of a subject, the output of the receiver, whether or not optionally frequency shifted to a higher frequency band, is transmitted via a conventional radio transmitter to a remote monitoring unit. Prior to transmission, the output of the photodetector may be applied to an audio mixer having as another input the output of a microphone placed in proximity to the subject being monitored. The output of the mixer is then transmitted to the remote receiver whereby a care giver can remotely monitor not only movements but also sounds produced by the subject being monitored.

The audio motion monitor of the present invention need not be adapted for remote reproduction of sound related to motion, but instead can be implemented for "in situ" sound production on the subject to which the monitor is attached or coupled. In such an embodiment, the monitor again includes a carrier, an optical fiber supported by the carrier and having an input end and an output end, a laser source for injecting coherent light beam into the input end of the fiber, a photoreceiver coupled to the output end of the fiber and illuminated by laser light transmitted through the fiber, the photoreceiver producing an output signal related to movements of the fiber, an amplifier for amplifying the output of the photoreceiver, or optionally, the output of a frequency shifter connected to the output of the photoreceiver, and a loudspeaker coupled to the amplifier and producing audible output sound related to modal noise produced at the output end of the optical fiber due to movement of the optical fiber. In this embodiment, the carrier typically is clothing worn by or attached to a living human or animal, a robot or robotic toy, a piece of machinery, or a vehicle. The result is the creation of an electronic noise sound that changes in response to and in relation to motions of the subject to which the optical fiber is attached by means of the carrier. The loudspeaker is either attached to the rest of the system on the carrier, or the sound is transmitted by radio or wires to a remote receiver amplifier and speaker.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
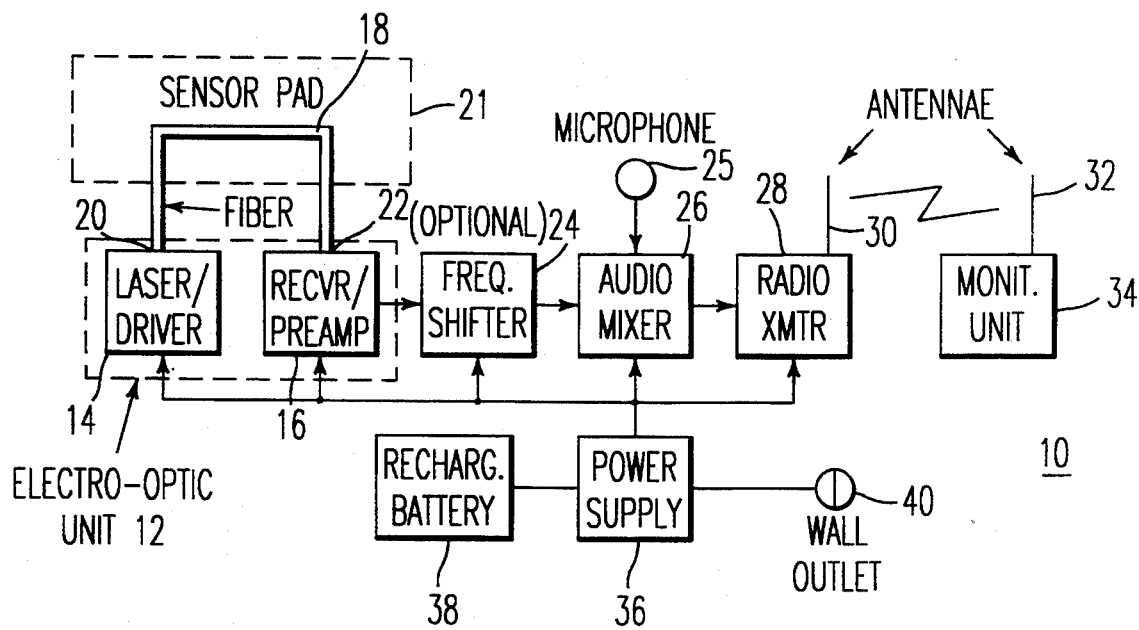
FIG. 1 is block diagram of a first embodiment of an audio motion monitor according to the present invention.

Referring now to the drawings, wherein like reference numerals designate identical or corresponding parts throughout the several views, and more particularly to FIG. 1 thereof, the audible motion monitor 10 of the present invention includes an electro-optic unit 12 including a laser with associated laser driver 14 (hereinafter called laser/driver 14) and a photoreceiver/preamp 16 composed of a photodetector, preferably a split detector as disclosed in pending U.S. patent application Ser. No. 07/975,853. Coupled to the electro optic unit 12 is a multi-mode optic fiber 18 having an input end 20 coupled to the laser in the laser/driver 14 and an output end 22 coupled to the photodetector in the photoreceiver/preamp 16. The fiber 18 is carried by a carrier 21, which is typically a flexible pad, made of cloth or some other soft material, in which the fiber 18 is interwoven or otherwise attached, either adhesively or by other conventional means so that the fiber 18 can be mechanically coupled to a subject or object by means of the carrier 21. For example, a fiber can be attached to a sheet of polyethylene plastic by first spraying the plastic and perhaps also the fiber with an adhesive and then pressing the fiber into place in the desired serpentine pattern. A second polyethylene sheet can then be attached to cover and encapsulate the fiber. Or the same method could be used to encapsulate a fiber between two sheets of cotton. Alternatively, the fiber can be laid down between two thin sheets of heat-sealable plastic in the desired serpentine pattern, and the two plastic sheets can be heated sealed together as the fiber advances, once again encapsulating the fiber between the plastic sheets. It can be seen that there are thus many different ways in which a fiber can be attached to a flexible material and used to practice the present invention.

The output of the receiver/preamp 16 is connected to a frequency shifter 24 having an output connected to an audio mixer 26, which in turn has an output connected to a radio transmitter 28. Radio transmitter 28 transmits via its antenna 30 to an antenna 32 of a monitor unit 34. The monitor unit 34 includes a receiver, amplifier and loudspeaker by which signals modulated and transmitted by the transmitter 28 are reproduced as sound by the monitor unit 34. The transmitter 28 and monitor unit 34 comply with Part 15 of FCC Rules and Regulations.

The invention illustrated in FIG. 1 is similar to that disclosed in the Applicant's prior U.S. applications above identified, in that the present invention likewise uses the modal noise induced in coherent light propagating in a multi-mode fiber in the presence of mechanical motions of a subject to detect motion or movement of the subject. Like the noted, earlier applications in the embodiment of FIG. 1, a fiber 18 is attached to a flexible pad or carrier 21 coupled to the subject and a laser 14 injects a coherent light beam into an input end 20 of the fiber 18. Light emerging from the output end 22 of the fiber 18 illuminates a receiver/preamp, optimally including a two-segment "split" photodetector, and optimally with some degree of spatial filtration but with any of the photodetector schemes taught in application Ser. No. 07/975,853, some of which are shown in FIGS. 3a–3j and discussed hereinafter.

The embodiment shown in FIG. 1 differs from the inventions disclosed in 07/975,853 and 07/802,868 in that no analysis is made of the modal noise signal for the purpose of extracting breath and heartbeat information as disclosed in the earlier applications, and in fact no analysis is made of the modal noise signal for any purpose. Instead, the modal noise sounds generated by motions of the subject are transmitted unchanged, or optionally frequency shifted as described below for purposes of increasing audible clarity, and optionally added to the audio signal detected by a conventional microphone 25 placed in proximity to the subject being monitored. The audio signal produced by the monitor unit 34 and heard by the care giver is thus the modal noise due to motions of the subject, optionally combined with routine sounds made by the subject. When the audio motion monitor of the present invention is applied to a human subject, the sound produced by the monitor and heard by the care giver will be sounds related to body motions, possibly including motions due to breathing and possibly including motions due to heartbeats or peristalsis as well.

When the modal noise signals due to motions of the subject are passed through an audio amplifier and loudspeaker with good low-frequency response, a noise-like signal is heard in which the amplitude and average frequency of the noise mimics the motion. It is straightforward to identify noises characteristic of gross motions (rolling over, for example), and distinguishing them from, for example, the more regular rushing sounds associated with breathing.

However, the modal noise signals have their greatest amplitude in the range of 0 to 200 Hz, a part of the audio spectrum below the portion of the audio spectrum to which the human ear is most sensitive, and also below the portion of the audio spectrum which is efficiently amplified and reproduced by inexpensive electronics and small-sized audio speakers typical of conventional normal remote monitors. In order to produce sound in a portion of the audio spectrum to which the human ear is more sensitive and in order to be able to employ inexpensive electronics and small-sized audio speakers, the present invention optionally includes the frequency shifter 24 shown in FIG. 1 to shift the modal noise signals up in frequency, using analog electronic or digital signal processing techniques, to a higher frequency band at which simple electronics and small diameter loudspeakers are relatively more efficient.

Thus, for example, the frequency shifter 24 may be implemented by means of an amplitude modulation circuit in which the modal noise signal is used to amplitude modulate a relatively strong signal at a higher frequency, for example, 500 Hz. The resulting signal will then contain the original modal noise spectrum (around 0 to 200 Hz), the 500 Hz carrier signal, and the sum and difference of the carrier and the modal noise spectrum. These latter two components will lie in the two side bands on either side of the 500 Hz carrier, one lying at higher frequencies (500 to 700 Hz), and the other inverted and lying on the lower side of the carrier (500–300 Hz). To render this signal comparable in a qualitative sense to the original modal noise signal (albeit shifted to a higher frequency), it is desirable to remove the original signal (0–200 Hz), the signal in the lower-side band (500–300 Hz), and the carrier at 500 Hz, leaving just the upper side band (500–700 Hz). This can be accomplished using well known filtration methods, either analog or digital. For example, a combination of a high-pass filter with a sharp cut-off at 500 Hz will remove the original noise signal plus the lower side band and much of the 500 Hz carrier. The rest of the carrier can even be more effectively removed, if necessary, by using a 500 Hz notch filter, another well known technique, As is evident to a person skilled in the electronics art, there are various ways to accomplish the frequency shifting performed by the frequency shifter 24. For example the signal at the output of the receiver/preamp 22 can be modulated onto a 100 kHz carrier, beat against a 99 kHz injected "local oscillator" signal, and filtered with a 1 kHz hi-pass filter, whereby the modal noise signal will be heard upshifted from the original 0–200 Hz frequency to 1.0–1.2 kHz.

As is illustrated in FIG. 1, the modal noise signal at the output of the receiver/preamp 16, whether or not optionally shifted by the frequency shifter 24, is optionally applied to an audio mixer 26, having as another input the output of the microphone 25. The microphone 25 is in turn placed in close proximity to the subject being monitored and serves to pick up sounds, such as baby crying, talking or other sounds existing within the vicinity of the subject being monitored for simultaneously listening by the care giver at the remote monitoring unit.

As shown in FIG. 1, the electronic components of the audible motion monitor of the present invention are powered by means of a power supply 36 adapted for use with a rechargeable battery 38 or line voltage from a wall outlet 40. Any conventional power source capable of producing the requisite voltage and current can be used.

Figure 2:
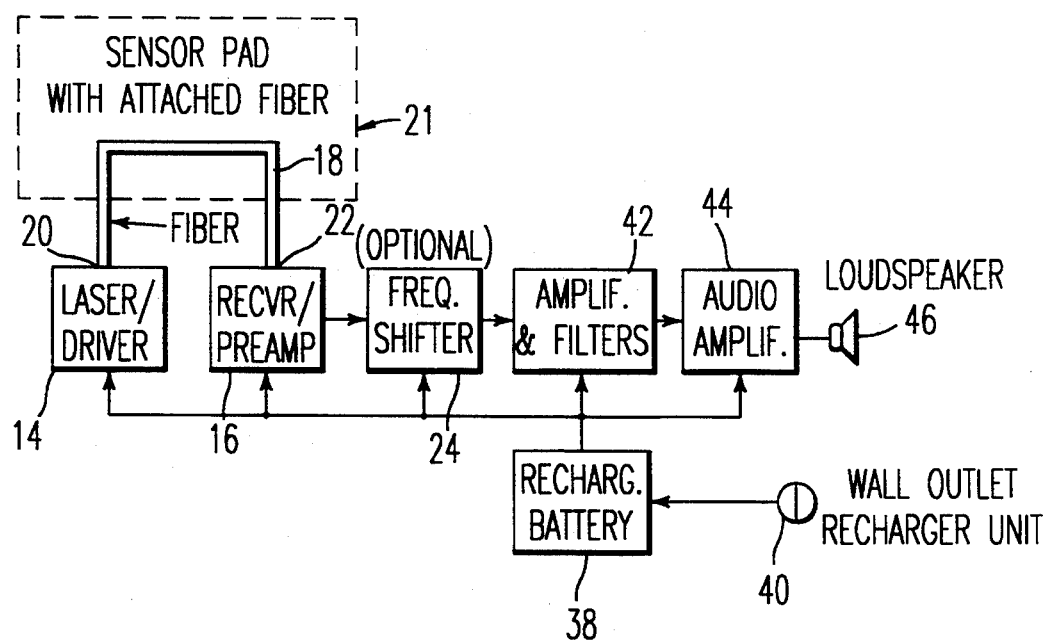
FIG. 2 is a schematic block diagram of the audio motion monitor of the present invention as applied to the in situ production of sound in relation to movement of the subject being monitored.

Another embodiment of the audio motion monitor of the present invention is illustrated in FIG. 2. In this embodiment, the optical fiber 18 is coupled to a subject, preferably by being embedded or attached to a carrier such as an article of clothing and the monitor is designed to produce sound at the location of the subject being monitored contemporaneous with movement of the subject. In this embodiment, the "subject" being monitored can be a living human or animal, a robot or robotic toy, a piece of machinery, or a vehicle of some sort. The modal noise signal produced at the output of the receiver/preamp 16, after optional frequency shifting and appropriate filtration and amplification in the amplifier and filter circuit 42, is played through a loudspeaker 46. The filter circuit 42 could be designed to emphasize those frequencies which enhance the interest or utility of the sound played by the loudspeaker 46. Other possible signal processing which can advantageously be applied at this point includes, without limitation, amplitude clipping or compressing/expanding of the sound amplitudes, sometimes called "companding" in the radio communications art. The loudspeaker 46 is either attached to the carrier 21 or is otherwise attached to the subject being monitored, or may be transmitted by radio or wires to a remote receiver, amplifier and speaker.

Without limiting the scope of the embodiment illustrated in FIG. 2, one application of the audible motion sensor therein illustrated is as a child's toy suit of "armor" fashioned for example of aluminized fabric to resemble body armor familiar to viewers of the "Terminator" or "Robocop" movie series and other movies about robots. As the subject moves about wearing the audible motion monitor of the present invention, the modal noise generated in the optical fiber can be heard from the loudspeaker 46, creating a unique "technological" sound that mimics the subject's motions and suggests a robot-like nature for the subject. Alternatively, a similar "suit of armor" incorporating the audio motion monitor of the present invention can be attached to a movable part of a mechanical toy, a robot, an animal, or a moving vehicle.

As with the first embodiment, in the embodiment of FIG. 2 coherent light from a diode laser 14 similar to those used in CD players illuminates the input 20 of the optical fiber 18 which is embedded or attached to the carrier 21. Preferably, the fiber 18 is a robust, low-cost plastic optical fiber. Light emerging from the output end 22 of the fiber 18 strikes a photodetector within the receiver/preamp 16, preferably a two-segment PIN photodiode differentially amplified, and preferably positioned with respect to the fiber end 22 so as to introduce an optimal degree of spatial filtration of the optical speckle pattern which emerges from the fiber 18, as taught in pending patent application Ser. No. 07/975,853. Any of the filter techniques, however, taught in Ser. No. 07/975,853 are applicable.

When the modal noise signals due to body or object motions are passed through the amplifier and filter circuit 42, and passed to the loudspeaker 46, a rumbling noise-like signal is heard in which the amplitude and the average frequency of the sound mimics the motions. Because of the sensitivity of the optical fiber modal noise to physical motion, the noises seem highly correlated to the motions, and the noises seem to be due to the motions.

As with the first embodiment, the second embodiment will work satisfactorily as described if the audio spectral response of the loudspeaker extends to sufficiently low audio frequencies. However, modal noise signals typically have their greatest amplitude, as above noted, in the range of 0 to 200 Hz. Thus, in the second embodiment of FIG. 2, as in the first embodiment of FIG. 1, it is advantageously optional to shift the modal noise for frequency signals up in frequency, using the frequency shifter 24 above described in relation to the FIG. 1 embodiment.

Figure 3A:
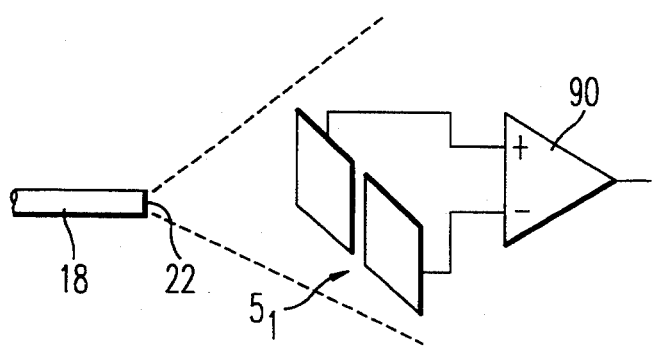
FIGS. 3a–3j are schematic sketches of different detection circuits which can be employed to detect the speckle light patterns according to the present invention.
Figure 3B:
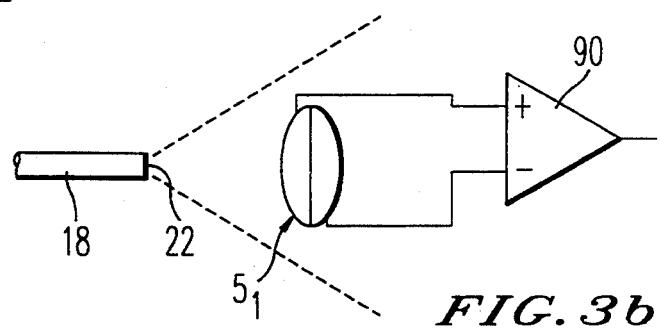
Figure 3C:
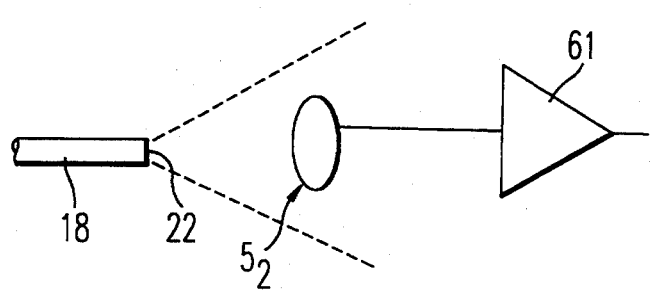

As described in Ser. No. 07/975,853, a preferred embodiment of a detection system used to detect the optical speckle pattern employs a two-element PIN photodetector $5_1$, a split detector commonly available with either rectangular elements as shown in FIG. 3a or hemicircular elements as shown in FIG. 3b, differentially connected to a differential amplifier 90 to provide common mode rejection and a doubling of the portion of the noise current due to intensity exchange between the photodetector elements, wherein the photodetector elements are positioned some distance away from the fiber output and so that they intercept a 33-100% fraction, preferably 45-83%, and optimally 60-70% of the speckle correlation cells. Correspondingly, if a single detector $5_2$ is used, as shown in FIG. 3c, a preferred embodiment of the single detection system places the photodetector spaced apart from the fiber output end 22 so that it likewise intercepts an optimal fraction, for example, 27-74% and optimally approximately 50%, of the speckle correlation cells, with the output of photoconductor $5_2$ being amplified by amplifier 61.

Figure 3D:
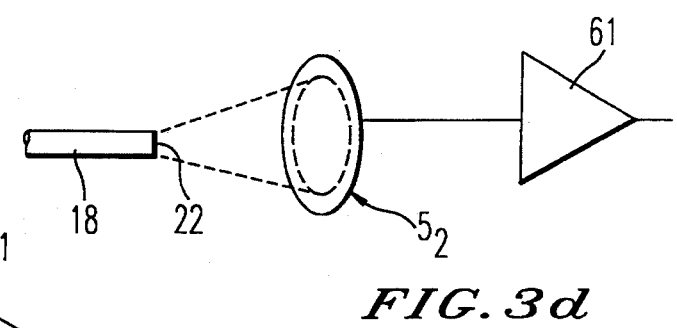
Figure 3E:
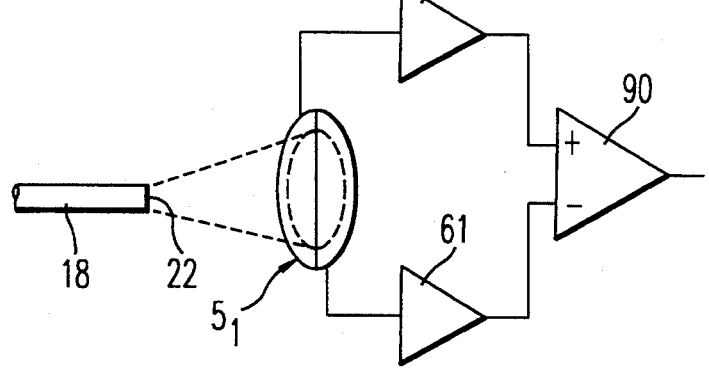

In addition to the preferred embodiments of the detection system above described, many different variations are also possible. For example, in a variation of the single detector system, the photodetector $5_2$ is positioned to collect all of the modal light from the output of the fiber, as shown in FIG. 3d. This technique is inefficient because it relies on exchange of the light between guided and unguided modes, a weak effect, and may have an efficiency of 5 to 20% of that of the preferred embodiments. Similarly, a split detector $5_1$, with differential detection detecting essentially all of the light on the two approximately equal photodetectors is also possible, as shown in FIG. 3e, but not as efficient as the preferred split detector embodiment. Further, the shapes of the detectors for either the split or the single detector embodiments do not affect performance. Separate rectangular, circular, or other-shaped photodetectors having about equal areas, or similar such split detectors, are equally effective.

Figure 3F:
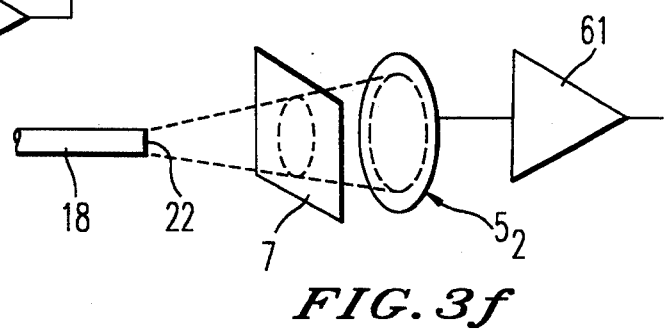
Figure 3G:
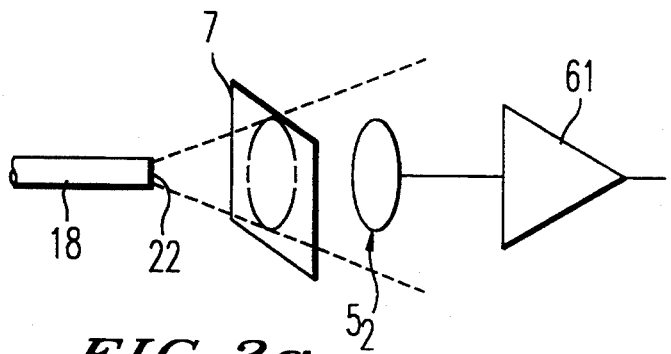
Figure 3H:
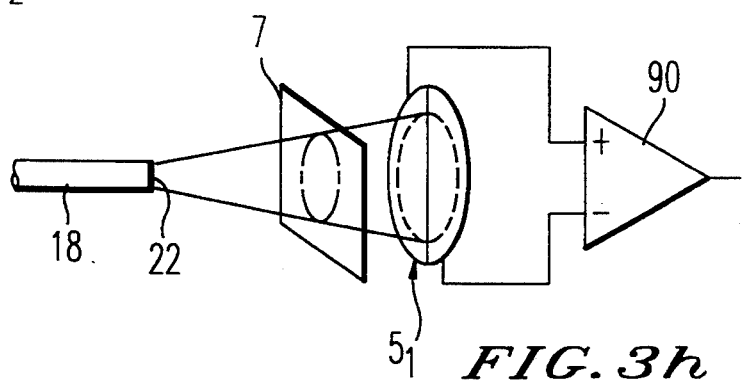
Figure 3I:
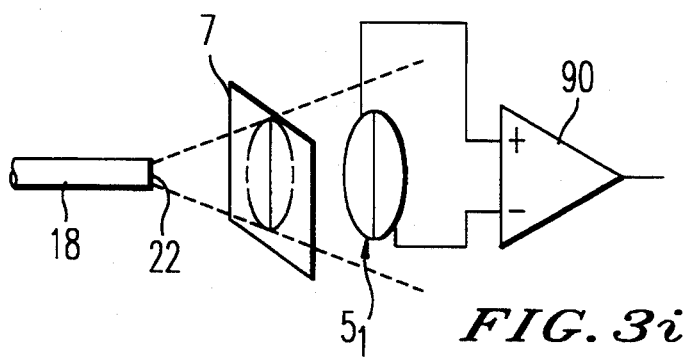

Similarly, as in the spatial filtering embodiment, a polarization filtration embodiment is also usable even if all the light which passes through the polarizer 7 is intercepted by the photodetector, as shown in FIG. 3f. Less efficient would be a small single detector $5_2$ which detects only part of the light passed through a polarizer 7, as shown in FIG. 3g, which generates noise in two ways, including an exchange between polarizations and an exchange with cells which miss the detector, because the combination reduces the percent of speckle striking the detector to less than the optimal 50%. Likewise, where a differential detector $5_1$ is employed in conjunction with a polarizer 7, as shown in FIG. 3h, noise is generated in two ways, firstly by exchange between the polarities, and secondly by exchange between the halves of the photodetector $5_1$ due to differential detection. Efficiency is unnecessarily low because the polarizer reduces the modes to 50%, below the optimal 66.7%, and also because the polarizer attenuates the light by about 20%. Where the photodetector $5_1$ is arranged to intercept only a part of the light passing through the polarizer 7, as shown in FIG. 3i, and where differential detection is employed, noise is generated in three ways, including exchange between the different polarizations, exchange between halves of the photodetector cells (differential detection), and exchange with cells which miss the detector; but the efficiency is again less than in either of the preferred embodiments because the combination of filtration methods over restricts the percentage of modes illuminating the detector.

Figure 3J:
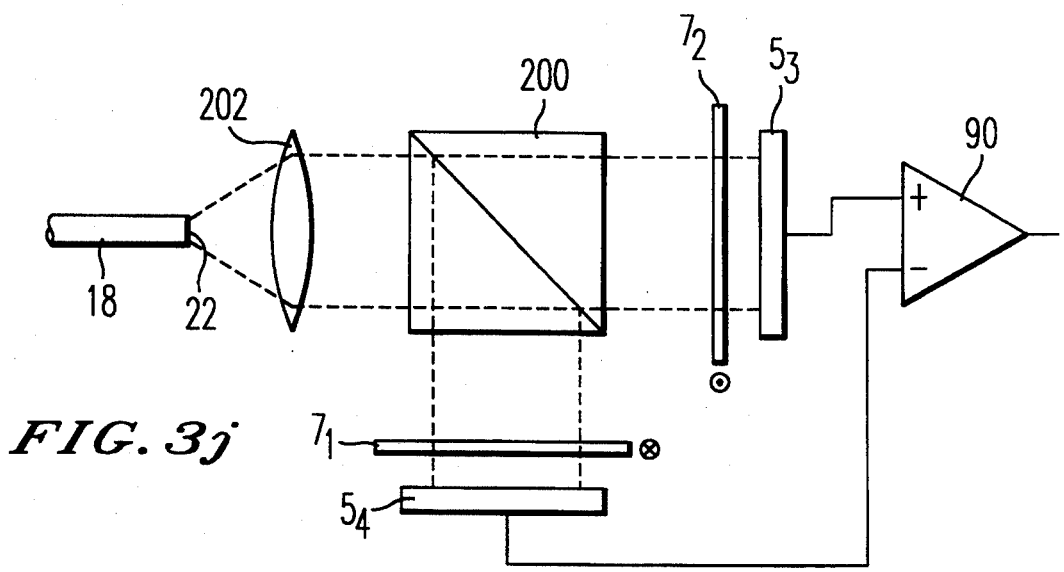

In yet another embodiment involving polarization filtration, as shown in FIG. 3j, use can be made of beam splitter prism 200 to split light from the output 22 of the fiber 18 into two paths. In this embodiment, a collimator lens 202, e.g., a microscope objective lens with a sufficiently large numerical aperture to not vignette the beam of light from the fiber, is introduced between the fiber optic end 22 and a nominally 50%-50% beam splitter prism 200 which splits the collimated light into two different beams of essentially equal power. Each path includes a polarizing filter, $7_1$ or $7_2$, the polarizations of which are crossed in orientation so that one filter passes light with one polarization orientation and the other passes light with the other polarization orientation, and light passing through the two polarizers impinges on respective photodetectors $5_3$, $5_4$ which are connected to a differential amplifier 90 for differential detection of the signals produced by the two detectors $5_3$, $5_4$. Thus, energy exchange between polarizations will give rise to substantial noise currents in the differentially detected output signal.

Further, as disclosed in Ser. No. 07/975,853, spatial filtering can be accomplished by inserting a Ronchi Ruling or knife edge between the fiber output end 22 and the photodetector.

Obviously, numerous modifications and variations of the present invention are possible in light of the above teachings. For example, in the second embodiment, the carrier 21 may be in the form of a cloth or foam pad or any other flexible material. The carrier 21 may be formed as a vest, leggings, arm coverings, etc., and may be provided with a belt, velcro or other means for attachment to the subject. The belt may also serve as a housing for the electronics and the loudspeaker 46. Additionally, any conventional transmitter/receiver systems can be used to implement the transmitter 28 and monitor unit 34, and other techniques are quite possible for implementing the frequency shifter 24. It is therefore to be understood within the scope of the appended claims, the invention may be practiced otherwise and as specifically described herein.

What is claimed as new and desired to be secured by Letters Patent of the United States is:

1. A motion monitor for producing audible sound, comprising:
    a flexible carrier;
    an optical fiber carried by the flexible carrier and having an input end and an output end;
    laser means for applying a light beam to the input end of the fiber;
    a photoreceiver including photodetector means coupled to the output end of the fiber and illuminated by laser light transmitted through the fiber for producing an output signal representative of modal noise developed in the optical fiber due to physical movement of the fiber; and
    sound producing means coupled to the photoreceiver for producing audible sound representative of modal noise produced at the output of the optical fiber due to movement of the optical fiber.

2. The monitor according to claim 1, wherein said photodetector means comprises:
a single photodetector positioned at a distance from the output end of said fiber so as to intercept 24–74% of the speckles of light transmitted at said output end.

3. The monitor according to claim 1, wherein said photodetector means comprises:
plural photoconductive elements disposed opposite the output end of said optical fiber so that said elements are illuminated by a speckle pattern of light transmitted through said fiber, said elements producing a pair of outputs each representing approximately half of the speckle pattern of light incident on said elements; and
differential amplifier means having a pair of inputs coupled to respective of the outputs produced by said plural photoconductive elements and an output which is a difference signal representing a difference between the outputs produced by said plural photoconductive elements.

4. The monitor according to claim 3, wherein said plural photoconductive elements are positioned at a distance from the output end of the optical fiber so as to intercept 33–100% of the speckles of light transmitted at said output end.

5. The monitor according to claim 4, wherein said plural photoconductive elements are positioned at distance from the output end of the optical fiber so as to intercept 45–83% of the speckles of light transmitted at said output end.

6. The monitor according to claim 5, wherein said plural photoconductive elements are positioned at a distance from the output end of the optical fiber so as to intercept 60–70% of the speckles of light transmitted at said output end.

7. The monitor according to claim 1, wherein said photoreceiver comprises:
filter means disposed between the output end of said optical fiber and said photodetector means for reducing the number of speckles of light applied to said photodetector means.

8. The monitor according to claims 1, 2, 3, 4, 5, 6 or 7, wherein said photoreceiver comprises:
frequency shifting means having an output coupled to said sound producing means for shifting in frequency the output of said photodetector means from a first frequency range to a second higher frequency range.

9. The monitor according to claims 1, 2, 3, 4, 5, 6 or 7, wherein said sound producing means comprises:
a microphone for detecting sound;
an audio mixer having a first input coupled to an output of said microphone and a second input coupled to an output of said photoreceiver, and an output;
transmitter means coupled to the output of said mixer for transmitting a radio signal to a remote location; and
monitor means for receiving the signal transmitted by said transmitter means and producing an audible sound corresponding to the signal input to the transmitter means by the mixer.

10. The monitor according to claim 8, wherein said sound producing means comprises:
a microphone for detecting sound;
an audio mixer having a first input coupled to an output of said microphone and a second input coupled to an output of said photoreceiver, and an output;
transmitter means coupled to the output of said mixer for transmitting a radio signal to a remote location; and
monitor means for receiving the signal transmitted by said transmitter means and producing an audible sound corresponding to the signal input to the transmitter means by the mixer.

11. The monitor according to claim 1, wherein said sound producing means comprises:
amplifier means for amplifying the output of said photoreceiver; and
a loudspeaker coupled to said amplifier means.

12. The monitor according to claim 11, wherein said photoreceiver comprises:
frequency shifting means having an output coupled to said sound producing means for shifting in frequency the output of said photodetector means from a first frequency range to a second higher frequency range.

13. The monitor according to claim 11, wherein said carrier comprises attachment means for attaching the carrier to a subject being monitored.

14. The monitor according to claim 11, wherein said carrier comprises means for mounting said loudspeaker on said carrier.

15. A system for producing motion related sound, comprising:
an object;
a flexible carrier coupled to said object;
an optical fiber carried by said flexible carrier and having an input end and an output end;
laser means for applying a laser beam to the input end of the optical fiber;
a photoreceiver including photodetector means coupled to the output end of said optical fiber and illuminated by laser light transmitted through the fiber for producing an output signal representative of modal noise developed in said optical fiber due to physical movement of said optical fiber; and
sound producing means coupled to the photoreceiver for producing audible sound representative of modal noise produced at the output of the optical fiber due to movement of the optical fiber.

16. The system according to claim 15, wherein said photodetector means comprises:
a single photodetector positioned at a distance from the output end of said fiber so as to intercept 24–74% of the speckles of light transmitted at said output end.

17. The system according to claim 15, wherein said photodetector means comprises:
plural photoconductive elements disposed opposite the output end of said optical fiber so that said elements are illuminated by a speckle pattern of light transmitted through said fiber, said elements producing a pair of outputs each representing approximately half of the speckle pattern of light incident on said elements; and
differential amplifier means having a pair of inputs coupled to respective of the outputs produced by said plural photoconductive elements and an output which is a difference signal representing a difference between the outputs produced by said plural photoconductive elements.

18. The system according to claim 17, wherein said plural photoconductive elements are positioned at a distance from the output end of the optical fiber so as to intercept 33–100% of the speckles of light transmitted at said output end.

19. The system according to claim 18, wherein said plural photoconductive elements are positioned at distance from the output end of the optical fiber so as to intercept 45–83% of the speckles of light transmitted at said output end.

20. The system according to claim 19, wherein said plural photoconductive elements are positioned at a distance from the output end of the optical fiber so as to intercept 60–70% of the speckles of light transmitted at said output end.

21. The system according to claim 15, wherein said photoreceiver comprises:
    filter means disposed between the output end of said optical fiber and said photodetector means for reducing the number of speckles of light applied to said photodetector means.

22. The system according to claims 15, 16, 17, 18, 19, 20 or 21, wherein said photoreceiver comprises:
    frequency shifting means having an output coupled to said sound producing means for shifting in frequency the output of said photodetector means from a first frequency range to a second higher frequency range.

23. The system according to claim 15, wherein said sound producing means comprises:
    amplifier means for amplifying the output of said photoreceiver; and
    a loudspeaker coupled to said amplifier means.

24. The system according to claim 22, wherein said sound producing means comprises:
    amplifier means for amplifying the output of said photoreceiver; and
    a loudspeaker coupled to said amplifier means.

* * * * *